United States Patent
Dixon, Jr. et al.

(10) Patent No.: US 9,392,820 B2
(45) Date of Patent: Jul. 19, 2016

(54) CONDOM CONTAINING UNDERWEAR

(76) Inventors: Darryl W. Dixon, Jr., West Bloomfield, MI (US); Dante A. Dixon, West Bloomfield, MI (US)

(*) Notice: Subject to any disclaimer, the term of this patent is extended or adjusted under 35 U.S.C. 154(b) by 0 days.

(21) Appl. No.: 13/467,120

(22) Filed: May 9, 2012

(65) Prior Publication Data

US 2013/0298913 A1 Nov. 14, 2013

(51) Int. Cl.
  *A61F 6/00* (2006.01)
  *A41B 9/00* (2006.01)
  *A41B 9/02* (2006.01)
  *A61F 6/06* (2006.01)
  *A61F 6/04* (2006.01)

(52) U.S. Cl.
  CPC ... *A41B 9/02* (2013.01); *A61F 6/00* (2013.01); *A61F 6/04* (2013.01); *A61F 6/065* (2013.01); *A41B 9/004* (2013.01); *A61F 2006/041* (2013.01)

(58) Field of Classification Search
  CPC ............ A61F 6/00; A61F 6/02; A61F 6/04; A61F 6/06; A61F 6/065; A61F 2006/041; A61F 2006/043; A61F 2006/044; A41B 9/00; A41B 9/001; A41B 9/004; A41B 9/02
  USPC ............ 128/830, 842, 844, 917, 918; 2/78.1, 2/78.2, 400, 403, 406, 408
  See application file for complete search history.

(56) References Cited

U.S. PATENT DOCUMENTS

| | | | | |
|---|---|---|---|---|
| 3,774,241 A | * | 11/1973 | Zerkle | 2/67 |
| 4,834,114 A | | 5/1989 | Boarman | |
| 4,870,958 A | * | 10/1989 | Webster | 602/67 |
| 4,966,165 A | * | 10/1990 | Anderson | 128/830 |
| 5,070,890 A | | 12/1991 | Papurt | |
| 5,158,556 A | | 10/1992 | Starley | |
| 5,172,430 A | | 12/1992 | Lerma-Solis | |
| 5,181,527 A | * | 1/1993 | Dorsey et al. | 128/830 |
| 5,209,241 A | * | 5/1993 | Hardy | 128/842 |
| 5,290,270 A | * | 3/1994 | Fisher | 604/387 |
| 5,460,188 A | * | 10/1995 | Barrett, Sr. | 128/842 |
| 5,535,757 A | | 7/1996 | Fleming, Jr. | |
| D384,487 S | | 10/1997 | Ingels | |
| 6,904,914 B2 | * | 6/2005 | Badgett | 128/842 |
| 7,100,213 B2 | * | 9/2006 | Krautbauer | 2/403 |
| 7,762,262 B1 | | 7/2010 | Granja | |

(Continued)

FOREIGN PATENT DOCUMENTS

| | | |
|---|---|---|
| EP | 0965314 A1 | 12/1999 |
| JP | 06075432 | 10/1994 |
| JP | 10243956 | 9/1998 |

(Continued)

OTHER PUBLICATIONS

International Search Report and Written Opinion mailed Aug. 23, 2013 for corresponding application PCT/US2013/039650 filed May 6, 2013.

*Primary Examiner* — Keri J Nelson
(74) *Attorney, Agent, or Firm* — Brooks Kushman P.C.

(57) ABSTRACT

A condom-containing underwear includes a body portion for receiving a wearer's waist and covering at least 30 percent of the wearer's abdominal area; and a condom portion connected to the body portion and for receiving a penis. The body portion may include a shell and a lining. The lining may be detachable from the shell. The condom portion may be collapsible such that it takes the form of a penis only upon a full insertion of the penis within the condom portion.

14 Claims, 6 Drawing Sheets

(56) References Cited

U.S. PATENT DOCUMENTS

2006/0137078 A1* 6/2006 Smaczny ........................ 2/400
2010/0071702 A1* 3/2010 Sturlingh ..................... 128/844

FOREIGN PATENT DOCUMENTS

| WO | WO0178536 | 10/2001 |
| WO | 2012011826 A1 | 1/2012 |

* cited by examiner

CONDOM CONTAINING UNDERWEAR

BACKGROUND

1. Technical Field

The present invention relates to a condom-containing underwear.

2. Background Art

Many types of condoms are known in the art. These conventional condoms tend to provide protection to a limited area of the genitals. As a result, these types of condoms have been met with limited use.

SUMMARY

In one embodiment, a condom-containing underwear includes a body portion for receiving a wearer's waist and covering at least 30 percent of the wearer's abdominal area; and a condom portion connected to the body portion and for receiving a penis. The body portion may include a shell and a lining. The lining may be detachable from the shell. The condom portion may be formed integral to the shell of the body portion. In certain designs, the condom portion may include an open end, a close end and an elongated tube for receiving the penis. In certain other designs, the condom portion may be collapsible and take the shape of a human's penis only upon a full insertion of the penis within the condom portion. The lining may be positioned between the wearer's skin and the shell. The shell may be positioned between the wearer's skin and the lining. The body portion may include an elastic opening for receiving the wearer's waist area. The body portion may be openable alongside the wearer's abdominal area.

A condom-containing underwear includes a body portion for receiving a wearer's waist and covering at least 50 percent of the wearer's abdominal area, the body portion including a shell and a lining; and a condom portion formed integral to the shell of the body portion and for receiving a penis. The condom portion may be collapsible with a non-extended length that is from 1.1 times to 5.5 times an average length of a penis.

DETAILED DESCRIPTION

As required, detailed embodiments of the present invention are disclosed herein; however, it is to be understood that the disclosed embodiments are merely exemplary of the invention that may be embodied in various and alternative forms. Specific structural and functional details disclosed herein are not to be interpreted as limiting, but merely as a representative basis for the claims and/or a representative basis for teaching one skilled in the art to variously employ the present invention. Moreover, except where otherwise expressly indicated, all numerical quantities in this description and in the claims indicating amounts of materials or conditions of reactions and/or use are to be understood as modified by the word "about" in describing the broadest scope of the invention.

Figure 1A:
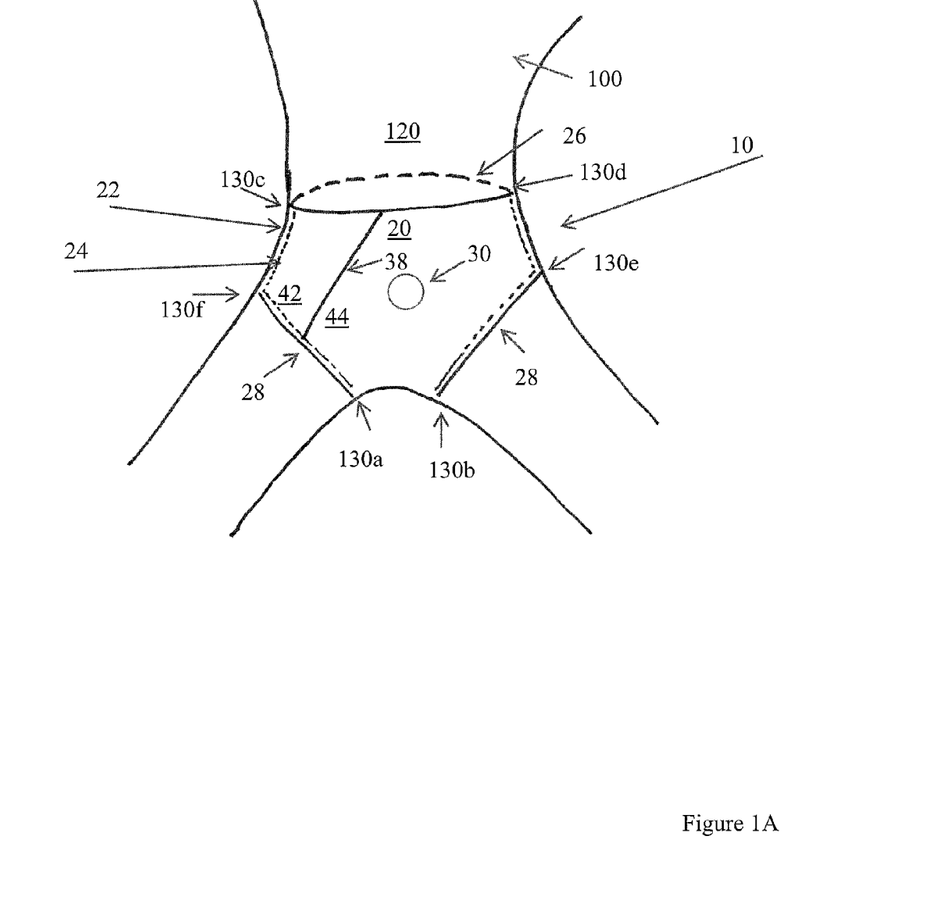
FIG. 1A illustratively depicts a perspective view of a condom-containing underwear according to at least one embodiment.
Figure 1B:
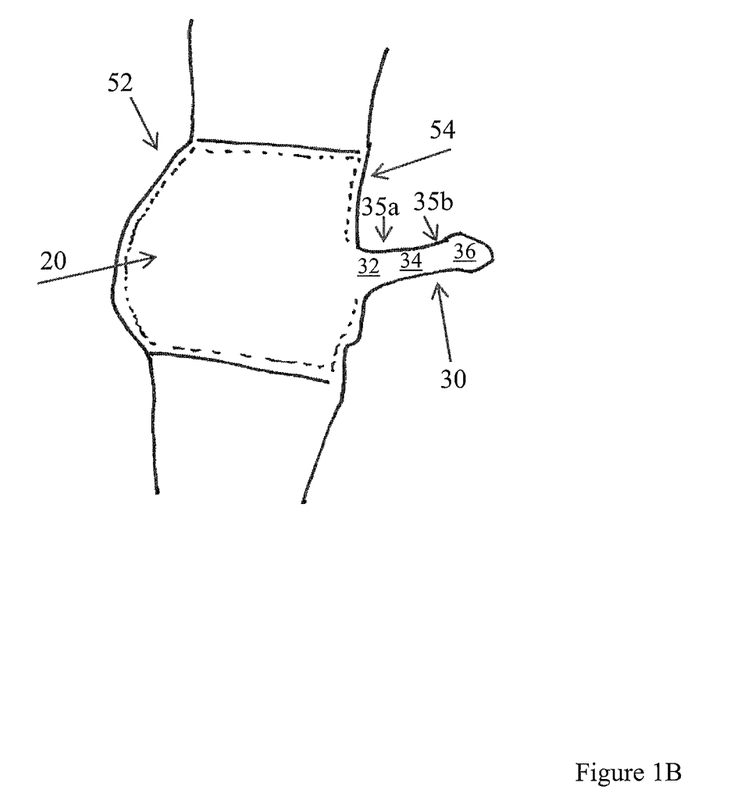
FIG. 1B illustratively depicts a side view of the condom-containing underwear of FIG. 1A.

In one embodiment, a condom-containing underwear generally shown at 10 is depicted in FIGS. 1A and 1B as modeled by a wearer 100. The condom-containing underwear 10 includes a body portion 20 for receiving the waist 120 of the wearer 100 and a condom portion 30 connected to the body portion 20. The body portion may be formed of a shell 22 and a lining 24. The condom portion 30 may be connected to the shell 22. In certain instances, the condom portion 30 and the shell 22 may be integral to each other and are formed, for instance, via molding, from the same material. The condom portion 30 may include an open end 32, an elongated tube 34 and a close end 36 for receiving and positioning the penis. The length and the cross-sectional dimension of the elongated tube 34 may be varied according to particular usage needs. When worn by a female, the condom portion 30 may be positioned at or near the vagina area and insertable into the vagina, as illustratively depicted in FIG. 3 described herein elsewhere.

Figure 3:
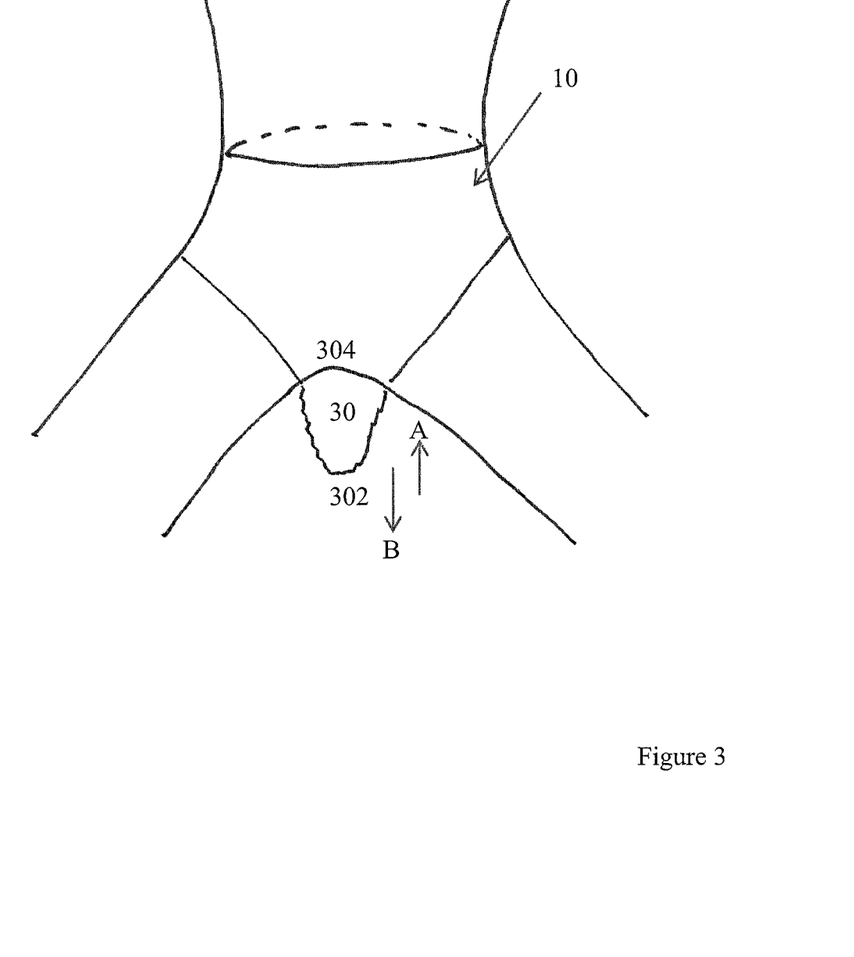
FIG. 3 illustratively depicts a front view of a condom-containing underwear according to at least yet another embodiment.

The condom portion 30 as illustratively referenced in FIG. 1B may be collapsible in much the same way described in relation to FIG. 3. While the collapsible condom portion 30 referenced in FIG. 3 may be positioned more suitable for being worn by a female wearer, the collapsible condom portion 30 referenced in FIG. 1B may be positioned more suitable for being worn by a male wearer. It is noted that in both scenarios, the condom portion 30 may be collapsible to the extent that it can be substantially shapeless or flat when in a rest position and can take the shape of a human penis upon full insertion of the penis within the condom portion 30.

The body portion 20 may include an elastic waist band 26 to make sure that the entire underwear 10 stays on the wearer 100 during session. Optionally the body portion 20 may include elastic thigh bands 28 to provide additional fastening.

The body portion 20 may be formed of a back part 52 and a front part 54. The front part 54 may be configured to cover at least 10 percent, 20 percent, 30 percent, 50 percent, 60 percent, 70 percent, 80 percent or 90 percent of the wearer's abdominal area. This level of coverage may be particularly useful, as the condom-containing underwear 10 can be used to reduce unnecessary exchanges of body fluids. This design is also useful as the condom-containing underwear 10 can be easily put on and taken off without having to incur unnecessary worries about material rupture and difficulties in positioning.

In one or more embodiments, the term "abdominal area" refers to an area of the wearer 100 bordered by a pubic line 130a-130b, a waist line 130c-130d at or near the navel 150, a left hip line 130d-130e, a right hip line 130c-130f, a left leg line 130e-130b, and a right leg line 130f-130a. The underwear 10 as depicted in FIG. 1A has a substantially full coverage of the abdominal area of the wearer 100. In suitable variations, that coverage can be reduced along one or more of the lines 130a-130b, 130c-130d, 130d-130e, 130c-130f, 130e-130b and 130f-130a, with a resulting abdominal coverage of at least 30 percent as described herein above.

In one or more embodiments, the term "buttocks area" refers to an area of the back part 52 of the wearer 100, which can be similarly defined as the case for the "abdominal area" discussed herein. In this connection, counterparts (not shown) of the lines 130a-130d, 130a-130b, 130a-130f and 130b-130e as located on the back part 52, along with the lines 130d-130e and 130c-130f, together border the buttocks area.

Although depicted in FIG. 1B to have a substantially coverage of the buttocks area, the body portion 30 may be substantially back-less. In this connection, the back part 52 may be configured to cover less than 80 percent, 70 percent, 60 percent, 50 percent, 40 percent, 30 percent, 20 percent, 10 percent, 5 percent, or 1 percent of the buttocks area. In certain instance, the back part 52 is essentially a string (not shown) connecting the waist line 26 and the crouch area.

Referring back to FIG. 1A, the body portion 20 may include one or more closable openings to help receive the waist 120. For instance, the body portion 20 may include first and second panels 42, 44. When in the state of being worn, the body portion 20 is configured to have the first and second front panels 42 and 44 contacting each other at connection 38, optionally via adhesive, strings or any other suitable materials and methods. The first and second panels 42, 44 may be positioned on and around the abdominal area or the back/buttocks area based one's preference. In those embodiments where the condom portion 30 is integral to the shell 22, the connection 38 may be positioned along or at one or both of the hip lines 130d-130e and 130c-130f. In this configuration, the first panel 42 may be of a different surface area relative to the second panel 44. With the one or more closable openings, the underwear 10 can look and function much like a baby diaper.

The body portion 20 can be in any suitable designs and/or be coupled with any suitable decorations. For instance, the body portion 30 may be shaped as a boxer short, a bikini, a "g" or "y" string type of underwear, athong, a low rise thong, a boy short, a floating crouch, a high hip brief, a high leg brief, a hip hugger, low rise cheeky, a bloomer, open on side hips, gym short side tie, side tie with bow, crouch-less in all styles, underwear with straps, low rise thong, skirt with attached panty skirt, and/or full oversize brief. For instance also, beads, laces, ruffles can also be added to enhance the looks.

Figure 2:
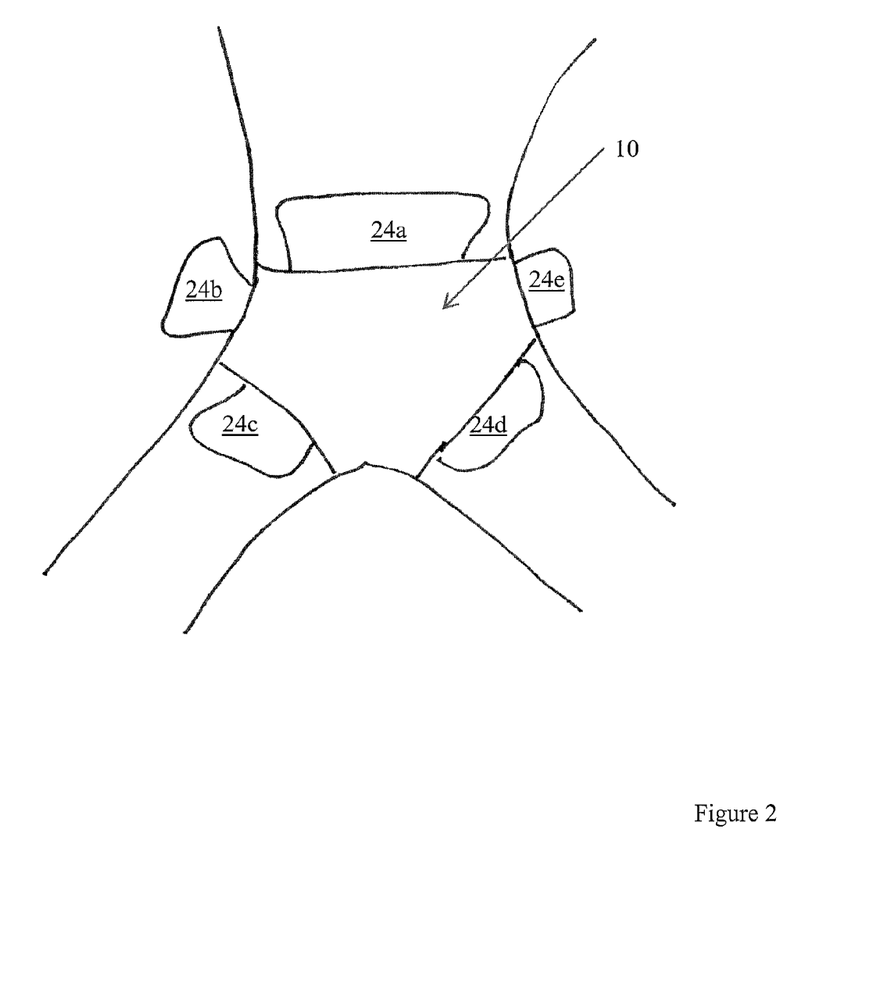
FIG. 2 illustratively depicts a front view of a condom-containing underwear according to at least another embodiment.

Although optional for the full utility of the underwear 10, the lining 24 helps provide an additional layer of comfort and protection against unwanted bodily fluids. The lining 24 can be used for quick emergency cleaning/absorption of bodily fluids such as male semen and female vaginal discharge. The lining can be used for post session quick cleaning, and leakage catching of spillage, and as absorption and extra protection during session. In this connection, the lining 24 can be used as a towelette and also provides internal comfort, extra layer protection, and can be folded out also. For the "folded out" designs, and as illustratively depicted in FIG. 2, the lining 24 can have a number of lining sections 24a, 24b, 24c, 24d and 24e, any one of which can be folded or pulled from the inside of the wearer, out to cover the thighs, up towards the stomach area, and used during/following a session. Although depicted in FIG. 2 as including 5 sections 24a to 24e, the lining 24 may include any suitable number of lining sections. The lining sections 24a to 24e can be completely detached from the underwear 10 upon pulling. Similar arrangement can be also employed for the back side 52 such that a number of lining sections similar to sections 24a to 24e can be pulled out from the back side 52. It serves also as a cleaning towel, following intercourse, when a cloth towel isn't available, prior to a full shower or bath. The lining 24 may be at least partially perforated to increase softness and flexibility. In the fully pulled out state, any one of the sections 24a to 24e may have a linear dimension of 12 to 24 inches.

When used, the lining 24 serves two main functions: to act as a soft cushion between the shell and the skin and hence to reduce friction-induced skin irritation, and to act as a secondary barrier against a possible fluid leak through its absorbency, in the unlikely event of a rupture in the shell 22.

When used, the lining 24 may be detachably connected to the shell 22 via any suitable ways. For instance, the lining 24 may be attached to the shell at the waistband area and/or the thigh band area via adhesives such as glue, sewing, soft cloth ties, or soft paper ties.

The lining 24 can be placed on an external side of the underwear 10 such that the shell 22 may be positioned between the skin and the lining 24. In this configuration, the lining can appear in different materials, different designs and different colors.

As stated herein, a unique feature of the underwear 10 is that the condom portion 30 may be seamlessly integral to the shell 22 such that unwanted bodily fluid exchange during session can be effectively reduced and avoided. In this connection, the shell 22 and the condom portion 30 can be formed as one piece, optionally formed by one step molding. This configuration provides sufficient protection while still ensuring flexibility when couples desire various positions during which bodily contact may be relatively more massive and chances of bodily fluid exchange may be relatively greater. This level of flexibility and protection cannot be readily achieved by certain conventional designs, including those with partial coverage for the scrotum and those with thin elastic bands to pull on the stand-alone condoms. These conventional designs not only suffer from the fact that coverage for the genitalia is partial wherein bodily fluids can creep through the boundaries onto one's skin, but also are deficient in being robust or sturdy, as stand-alone thin waist strings can easily tangle before, during and after the session which inevitably results in unnecessary stress and dissatisfaction. The designs with thin stand-alone waist strings also suffer from the fact that they tend to easily break and/or detach from the condom, and therefore, result in less satisfaction.

The present invention, according to one or more embodiments, is advantageous in reducing the risk of contracting certain disease-causing pathogens during and after active session. Non-limiting examples of such diseases include chlamydia, herpes, papilloma, syphilis, gonorrhea and the like. The use of the condom-containing underwear 10 according to one or more embodiments may also help prevent one or more of the following skin disorders such as infected ingrown pubic hairs, pimples, blackheads, boils, rashes and dermatitis.

The shell 22 and the lining 24 can each be formed of any suitable materials. The shell 22 can be formed to have its features be focused on its relatively good impermeability to fluids and relatively good elasticity and flexibility. Non-limiting materials for forming the shell 22 may include latex, vinyl, plastic, nitrile, silk, cotton, polyester, rayon, polymer such as polyurethane, and leather material such as sheepskin. The lining 24, on the other hand, can be formed to have its features be focused on its relatively good absorbance and softness. Non-limiting examples of the materials for the lining 24 may include cottons, silk, wool, polyester, rayon, tissue, and all varieties of paper materials.

The condom-containing underwear is particularly useful for certain population wherein contact in bodily fluids should by all means be avoided. Historically people with genitalia skin lesions, often due to the lesions being contagious in nature and/or one's psychological unwillingness or less tendency for an exposure of the area of the lesions, these people often refrain from having intercourse against their inner desires. Now with the underwear-style condom according to one or more embodiments of the present invention, these people can feel more socially desirable and sexually satisfied.

The condom portion 30 can be formed of material(s) of variable thicknesses along the longitudinal axis of the condom portion 30. This can be advantageous in minimizing potential condom breakage and also maintaining reasonable amount of enjoyment. In certain instances, a material or material wall thickness of the condom portion at the open end 32 is different from, and likely greater than, a material or material wall thickness of the condom portion at the closed end 36. It is also possible, and based upon certain needs, the material wall thickness of the open end 32 is smaller than the material wall thickness of the close end 36. Between the open end 32 and the close end 36, material wall thickness may vary gradually between the ends 32 and 36. For instance, a material wall thickness of a part 35a positioned between the open end 32 and the close end 36 may be of a value between the material wall thickness values of the ends 32 and 36, respectively. A material wall thickness of a part 35b positioned between the part 35a and the close end 36 may be of a value between the material wall thickness values of the part 35a and the close end 36, respectively.

The underwear 10 may include a second condom portion, optionally positioned for anal access. Dependent on the particular usage and session needs, the first condom may be designed for vaginal access and the second condom portion may be designed for anal access. Compared to the first condom portion, the second condom portion may be afforded with greater thickness and more durability.

In a different embodiment, the condom-containing underwear can be configured to be worn by a female. The female version can be substantially same in design and material compared to the male version 10 shown in FIG. 1A and FIG. 1B. When used as a female version, the underwear 10 may have a variety of condoms including a collapsible model that will take the form of the male penis for vaginal entry. Because the condom is attached to the body portion all in one piece, any contact, or the male penis being removed and entering the vagina unprotected can be effectively reduced. It won't get jabbed into the vagina, which may require a search into the vagina with the male or female hands.

In certain designs, the condom-containing underwear may be of a loose condom style. The loose condom style fits into the crotch area. As illustratively depicted in FIG. 3, the condom portion 30 can be in the form of a collapsible condom. The condom portion 30 may stay crinkled and fully collapsed when not in use and may be extended upon the insertion of the penis. When used by a male, the condom portion 30 may extend outwardly in the direction of "B" away from the crotch area; and when used by a female, the condom portion 30 may extend inwardly in the direction of "A" directed to the vagina. The extent of the collapsibility may vary depending upon a wearer's preference. In certain instances, the collapsible condom portion 30 may have a non-extended length that is no less than 1.1 times, 1.5 times, 2.0 times or 2.5 times, and no greater than 5 times, 4.5 times, 4 times, 3.5 times or 3 times the length of the penis, the non-extended length may be measured from the center of the crotch area 304 to the tip 302 of the condom portion. When fully extended, the collapsible condom portion 30 may be of a length that is no less than 1.1 times, 1.5 times or 2 times, and no greater than 3.5 times, 3.0 times or 2.5 times the non-extended length. In the loose condom style, the condom-containing underwear can lay open like a plastic wrap to provide a loose fit, and does not necessarily require being rolled out onto a penis on the male model, and allows gradual insertion of the penis into the vagina. In this connection, the flat condom style takes the shape of and surrounds the penis as insertion continues. Therefore the flat condom style is "unfitted" and lays substantially flat until the penis is inserted. The flat condom style is advantageous, at least because it does not squeeze the perimeter of the penis, thereby reducing the risk of the penis being cut short on blood flow and hence possibly increasing the pleasure level of a session. When positioned on the female model, the flat condom design can be placed in her crotch area, which then can be led into the vagina upon penis insertion.

For the female version, the condom portion will be pushed into the vagina during the session. In this connection, although not necessary, it might be preferable to have the shell and the condom portion being integral to each other as a single piece with continuity in material. This serves to reduce the chances of the shell being detached from the condom portion. If the detachment happens, the condom portion may be left within the vagina, the consequences of which are neither pleasant nor desirable.

As can be seen with the descriptions stated herein, the condom-containing underwear according to one or more embodiments prevents sliding off, provides full lower abdominal protections, and eliminates exchange of any body fluids. This benefits the male and female by providing better protection, dependable, and greater likelihood of staying on, and provides greater safety, disallowing vaginal leakage onto the male scrotum. The body fluids may include female fluid into the male condom or the pubic hair area, which could possibly contain open pores or cuts, scrapes, lesions, burns or any opening where bodily fluid exchange could take place. What can also be prevented is post male sperm leaks onto or near his female partner.

The condom-containing underwear according to one or more embodiments is advantageous for reducing fluid exchange during intense and creative positions during "intense athletic maneuvers" associated during sex, whereas the compared to model can possibly be maneuver off from the snaps and away.

The condom-containing underwear may include a spermicide at or near the condom portion. Non-limiting examples of the spermicide include Nonoxynol 9 and the spermicide can be of different varieties including creams, gels, foams, powders or liquids. The spermicide may be placed on the underwear prior to, during and after the session. The spermicide may also be provided in a small package placed next to or right on the underwear via a receiving-pocket.

The condom-containing underwear according to one or more embodiments of the present invention can cover the entire male and female lower abdomen and crotch area, preventing any possible leakage and contact between both parties. It is important to note, on female specific brands with the flat model collapsible models, the condom portion does not have to be rolled out.

The condom-containing underwear may help maintain the erection since the penis can be easily removed and repositioned, wherein sufficient blood flow recirculation into the penis can be permitted to continue on the sexual activities. The traditional condom squeezes the penis. Since the "unfitted/loose" condom portion of our model does not have to squeeze the penis, the "unfitted" loose condom provides less tightness or constriction around the penis, facilitate greater blood circulation, and reduces lost erections. In addition, traditional condoms are not likely to be reused since once they are rolled out it is not ordinarily easy to return them into their original rolled position. This on-time use of traditional condoms also translates to unnecessary cost and lost satisfaction. The loose/flat condom will stay in the vagina on the female models, and allow the male erection to return, minimizing the necessity to use another condom of any sort. The flat condom style described herein according to one or more embodiments of the present invention overcomes certain deficiencies of the traditional condoms. Of course, the condom portion 30 may optionally be configured to snuggly cover the penis as a traditional condom would, and in certain instances may snuggly cover the entire penis or at least a portion of the penis such as the first 2 to 3 inches of the penis.

The condom-containing underwear and lingerie set may include two or more condoms. Some of our designs may have multiple condoms on both sides, total of eight in some instances. If one condom breaks, lining can be used to seal the hole, and continue without removal, until the unit can be hopefully changed. Extra attached condoms provide extra insurance during session.

Figure 4A:
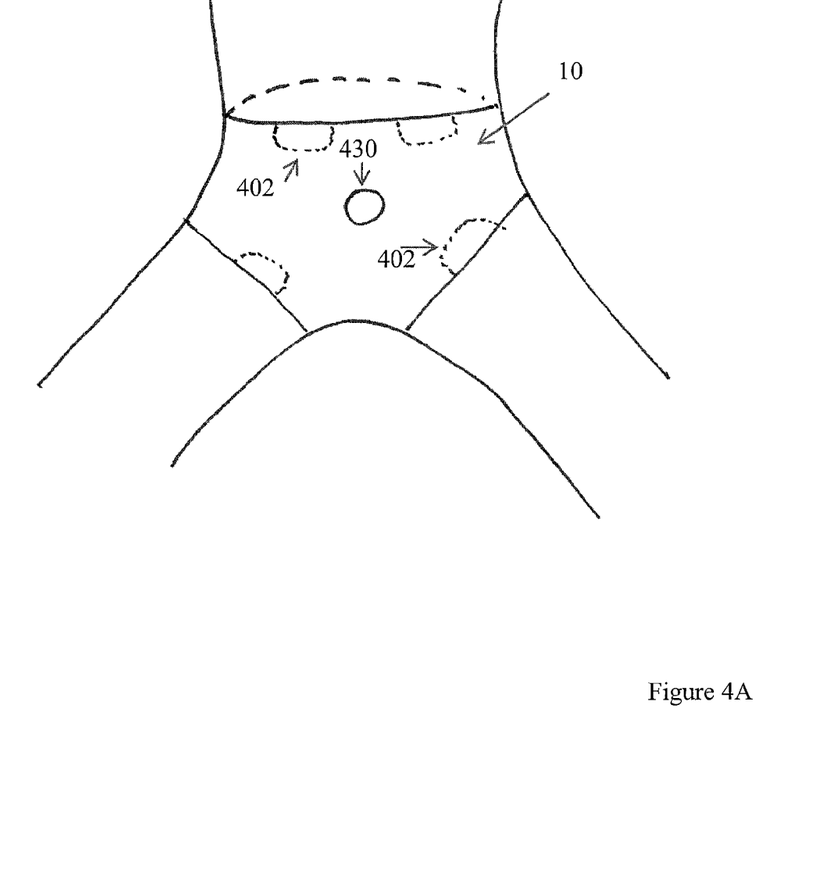
FIG. 4A illustratively depicts a front view of a condom-containing underwear according to at least another embodiment.

As illustratively depicted in FIG. 4A, the underwear 10 may include one or more receiving pockets 402 to store extra condoms, which can be any traditional condoms available commercially. The receiving pockets 402 may be defined between the shell 22 and the lining 24. The receiving pockets 402 may be located in any suitable positions on the underwear 10 and may be of any suitable numbers. The receiving pockets 402 can be located in the front and the back, on the sides, and around the legs, in which the condoms can fit snuggly. In this design, the underwear 10 includes a hole 430, without the condom portion 30 depicted in FIG. 1, for receiving the penis. The wearer may decide during session if a condom is needed and when the condom is needed, he may easily retrieve a condom from one of the receiving pockets 402 and apply accordingly. Unused condoms can be removed from the underwear 10 and saved for future use.

Figure 4B:
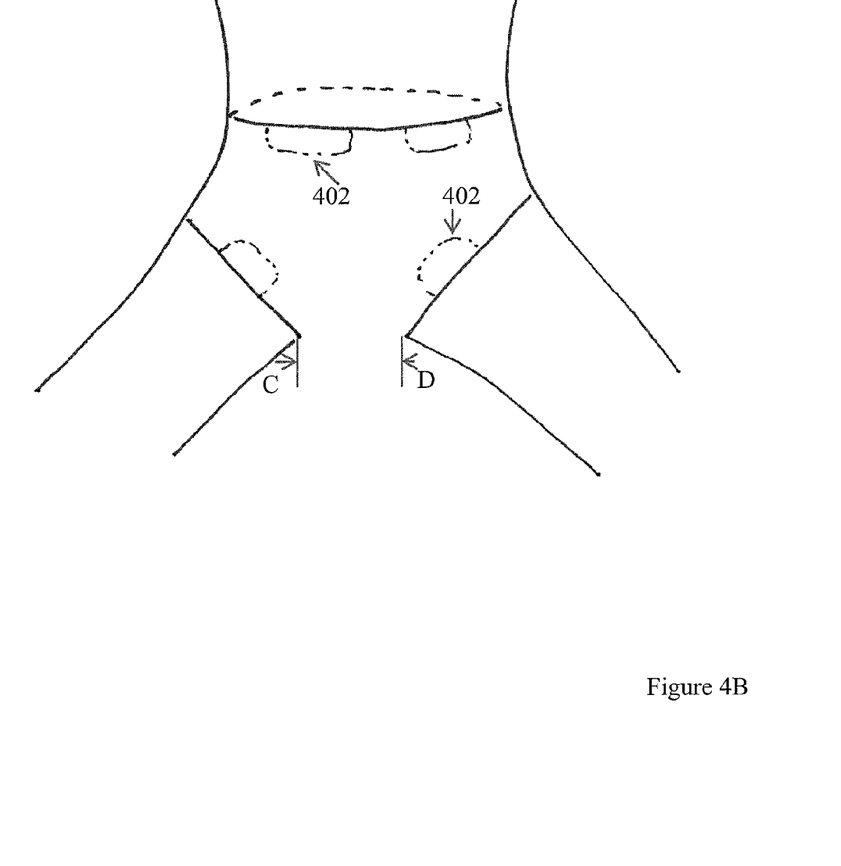
FIG. 4B illustratively depicts a front view of a variation to the condom-containing underwear referenced in FIG. 4A.

As a variation to the underwear of FIG. 4A, FIG. 4B depicts a crouch-less underwear to be worn by a female. In this variation, the area defined between potions "C" and "D" may be left open for receiving a partner's penis, while condoms may be conveniently retrieved from one of the receiving-pockets 402.

The condom-containing underwear 10 may further include one or more matching pieces including bras, slips, camisoles, nighties, and pajama wear.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A condom-containing underwear comprising:
   a body portion having a waist region defining a waist opening for receiving a waist of a wearer and covering at least a portion of an abdominal area of the wearer, the body portion including an outer shell defining a frontal region, a rear region, and a pair of leg opening regions each defining a leg opening for receiving legs of the wearer;
   a plurality of inner lining portions removably attached from an inner surface of the frontal region of the outer shell along one edge of each respective inner lining portions, wherein the plurality of inner lining portions are configured to be positioned between the outer shell and the wearer in a first portion and the inner lining portions are configured to fold away from the outer shell along each respective edge in a second position, the inner lining portions including an absorbent material suitable for cleansing, wherein two of the plurality of inner lining portions are removably attached adjacent the leg openings of the outer shell and are sized such that the two of the plurality of inner lining portions are foldable through the leg openings, and wherein one of the plurality of inner lining portions is removably attached adjacent the waist region and is sized such that the one of the plurality of inner lining portions is foldable through the waist opening, wherein the plurality of inner lining portions are configured to increase the surface contact area with the wearer when the inner lining portions are folded through the leg openings and the waist opening in the second position;
   a collapsible condom portion formed in an opening of the shell of the body portion for receiving a penis, wherein the condom portion is collapsed when not in use and is capable of extending into the body portion and away from the body portion to enable the condom-containing underwear to be suitable for unisex applications; and
   at least one pocket formed in and by the body portion for containing at least one supplemental condom configured to be attachable to the penis about the opening.

2. The condom-containing underwear of claim 1, wherein the body portion is adapted to cover at least 50 percent of the wearer's buttocks area.

3. The condom-containing underwear of claim 1, wherein the body portion is adapted to cover at least 50 percent of the wearer's abdominal area.

4. The condom-containing underwear of claim 1, wherein the shell and the inner lining portions are of different materials.

5. The condom-containing underwear of claim 1, wherein the body portion is adapted to cover no more than 90 percent of the wearer's buttocks area.

6. The condom-containing underwear of claim 1, wherein the condom portion is integral to the shell of the body portion.

7. The condom-containing underwear of claim 1, wherein the body portion is openable alongside the wearer's waist.

8. The condom-containing underwear of claim 1, further comprising a second condom portion.

9. The condom-containing underwear of claim 1, wherein the condom portion includes an open end, a close end and an elongated tube for receiving the penis.

10. The condom-containing underwear of claim 9, wherein the close end of the condom portion has a first wall thickness and the open end of the condom portion has a second wall thickness different from the first wall thickness.

11. The condom-containing underwear of claim 10, wherein a part of the condom portion between the open and close ends has a wall thickness between the first and second wall thicknesses.

12. The condom-containing underwear of claim 1, wherein the condom portion is collapsible with a non-extended length that is from 1.1 times to 5.5 times an average length of a penis.

13. The condom-containing underwear of claim 12, wherein the non-extended length of the condom portion is from 2.0 times to 5.5 times an average length of a penis.

14. The condom-containing underwear of claim 12, wherein the condom portion has an extended length that is from 1.1 times to 3.5 times the non-extended length.

* * * * *